United States Patent [19]

Ladd

[11] 4,336,254

[45] Jun. 22, 1982

[54] GUANIDINOPYRIMIDINE COMPOUNDS, COMPOSITIONS AND METHOD OF USING AS A DIURETIC

[75] Inventor: David L. Ladd, Overbrook Hills, Pa.

[73] Assignee: SmithKline Corporation, Philadelphia, Pa.

[21] Appl. No.: 247,048

[22] Filed: Mar. 24, 1981

[51] Int. Cl.$^3$ ............... A61K 31/505; C07D 239/30; C07D 239/48; C07D 239/50
[52] U.S. Cl. .................................... 424/251; 544/323
[58] Field of Search ....................... 544/323; 424/251

[56] References Cited

U.S. PATENT DOCUMENTS

| | | | |
|---|---|---|---|
| 2,295,563 | 9/1942 | D'Alelio et al. | 544/323 |
| 2,422,887 | 6/1947 | Curd et al. | 544/325 |
| 2,487,569 | 11/1949 | Mackey | 544/323 |
| 3,284,188 | 11/1966 | Amagasa et al. | 544/323 |

FOREIGN PATENT DOCUMENTS 408026 9/1966 Switzerland.

OTHER PUBLICATIONS

Boggiano, et al. "J. Pharm. & Pharmacol.", vol. 13, 1961, pp. 567–574.
King et al., "J. Chem. Soc.", 1947, pp. 726–734.
Carbon, "J. Org. Chem.", vol. 26, 1961, pp. 455–461.
Buehler et al., "Chem. Ber.", vol. 99, 1966, pp. 2997–3007.

Primary Examiner—Donald G. Daus
Assistant Examiner—James H. Turnipseed
Attorney, Agent, or Firm—William H. Edgerton; Richard D. Foggio; Alan D. Lourie

[57] ABSTRACT

2,4-Amino, guanidinopyrimidines have diuretic activity. A representative species of these compounds is 2-guanidino-4-amino-6-chloroguanidine which is prepared by the stepwise replacement of first the 2-halo of a 2,4,6-trihalopyrimidine by guanidino and then the 4-halo by ammonia.

11 Claims, No Drawings

GUANIDINOPYRIMIDINE COMPOUNDS, COMPOSITIONS AND METHOD OF USING AS A DIURETIC

This invention comprises a new series of chemical compounds whose basic structures have a pyrimidine ring with a guanidino substituent at least at one of the 2 or 4 positions. When a guanidino is present at only one of the 2 or 4 positions of the pyrimidine ring, an amino group should be present at the other. The compounds have diuretic activity and, more precisely, naturetic activity.

DESCRIPTION OF THE PRIOR ART

Certain highly substituted amino-guanidinopyrimidines are known to the art; B. G. Boggiano J. Pharm. and Pharmacol. 13 567 (1961) or Swiss Pat. No. 408,026 (Derwent No. 24,036). N-Unsubstituted guanidinopyrimidines have been described as chemical intermediates; F. E. King J. Chem. Soc. 1947 726, J. A. Carbon, J. Org. Chem. 26 455 (1961) or E. Buehler et al., Chem. Ber. 99 2997–3007 (1966). None of these publications suggest the substitution pattern present in the structures of the guanidinopyrimidines of this invention or the resulting biological activity.

DESCRIPTION OF THE INVENTION

The compounds of this invention are represented by the following structural formula:

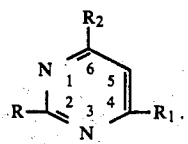

in which:
$R$ and $R_1$ are guanidino

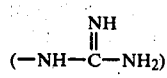

or amino, at least one being guanidino; and
$R_2$ is hydrogen, halo such as fluoro, chloro, bromo and iodo or amino.

A subgeneric group of compounds of this invention are those of structure I in which either $R$ or $R_1$ is guanidino, the other being amino and $R_2$ is chloro or amino.

Also included in this invention are the pharmaceutically acceptable acid addition salts of the bases of structural formula I above with nontoxic inorganic or organic acids such as hydrochloric, hydrobromic, hydriodic, sulfuric, phosphoric, sulfamic, ethane disulfonic, methanesulfonic, acetic, maleic or nitric acids. The salts can be prepared conveniently by mixing a lower alkanol solution of the base with an excess of the acid such as reacting a methanolic solution of the base with ethereal hydrogen chloride.

The compounds of this invention are prepared by stepwise replacement of the reactive halo substituents on a 2,4-halo or a 2,4,6-trihalopyrimidine. The nucleophilic reactant of the reaction is either ammonia or guanidine and the halo is usually chloro or bromo. The nucleophilic reactant, in at least one molar equivalent, is reacted with the halopyrimidine in a suitable organic solvent at from room temperature for the easily replaced halo substituent at the 2-position up to 115° under confined pressure conditions for 16 hours for the halo at the 6-position.

The stepwise reaction is represented by the following key steps:

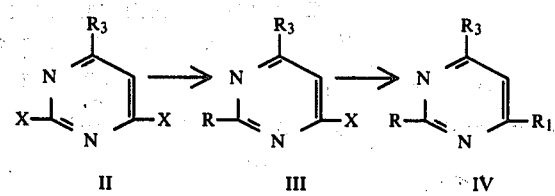

in which X is a reactive halo especially chloro or bromo, $R_3$ is hydrogen or a reactive halo and $R$ and $R_1$ are as defined above.

Of course when $R_3$ is a reactive halo it can be reacted further with the nucleophilic reagent to give 6-substituted 2,4-amino, quanidinopyrimidines or can be removed to give the 6-hydrogen series of compounds.

The compounds of this invention have diuretic activity which can be demonstrated in standard pharmacological tests. More specifically these compounds have naturetic activity in the sodium deficient rat test. Generally naturetic activity was demonstrated in this test at about 30 mg/kg with these new compounds. Standard diuretic compounds such as hydrochlorothiazide or triamterene show activity at 5 or 15 mg/kg respectively.

Certain of the compounds of this new series also show decreased potassium excretion especially at higher doses indicating a potassium sparing diuresis. Examples of these are the compounds whose structures have either a halo or amino substituent at position 6 of the pyrimidine ring.

Following is the protocol of the sodium deficient rat test and representative results obtained by using compounds of this invention as active ingredients.

Normal male rats weighing 175–203 g are placed on a sodium deficient diet for a period of 5 days. On the morning of the 5th day food is removed for the duration of the experiment. On day 6, water is also removed and the rats are loaded with 3.0 ml of 0.85% sodium chloride (s.c.) and 5 ml of water (p.o.). There are 8 animals in the control group and in each test group. The test compound is given orally. Urine samples are collected 6 hours after dosing.

TABLE I

| Compound | Dose mg/kg Salt | Dose mg/kg Base | No. of Rats | Electrolytes excreted uEg/rat Na⊕ | Electrolytes excreted uEg/rat K⊕ | Na⊕/K⊕ ratio |
|---|---|---|---|---|---|---|
| 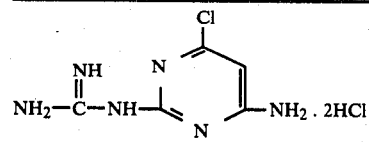 NH₂—C(=NH)—NH—[4-Cl-pyrimidin-2-yl]—NH₂ · 2HCl | 7.0 | 5.0 | 8 | 3 | 48 | 0.063 |
| | 13.9 | 10.0 | 8 | 2 | 42 | 0.047 |
| | 20.9 | 15.0 | 8 | 4 | 38 | 0.097 |
| | 41.7 | 30.0 | 8 | 52* | 65 | 0.825* |
| Control | — | — | 8 | 7 | 54 | 0.139 |
| | 15.0 | 10.8 | 8 | 1 | 57 | 0.023 |
| | 30.0 | 21.6 | 8 | 101* | 115 | 0.867* |
| Control | — | — | 8 | 9 | 97 | 0.094 |
| | 20.9 | 15.0 | 8 | 39* | 87 | 0.422* |
| | 41.7 | 30.0 | 8 | 105* | 87 | 1.272* |
| Control | — | — | 8 | 1 | 63 | 0.023 |
| | 83.4 | 60.0** | 8 | 49* | 42 | 1.181* |
| | 166.9 | 120.0** | 8 | 58* | 24* | 2.379* |
| Control | — | — | 8 | 8 | 81 | 0.146 |
| Other selected positive data from similar tests: | | | | | | |
| 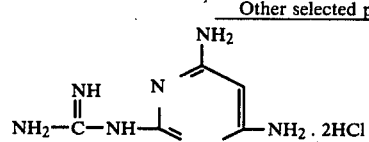 NH₂—C(=NH)—NH—[4-NH₂-pyrimidin-2-yl]—NH₂ · 2HCl | | 10 | 8 | 13.98* | 91.67 | 0.168 |
| | | 15 | 4 | 9.72 | 108.86 | 0.089 |
| | | 30 | 8 | 70.12* | 115.65 | 0.563* |
| | | 60 | 8 | 63.14* | 74.71 | 0.845* |
| | | 120** | 8 | 283.01* | 61.86 | 4.611* |
| 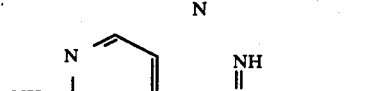 NH₂—[pyrimidin-2-yl]—NH—C(=NH)—NH₂ · 2HCl | | 30 | 8 | 14* | 75 | 0.186 |
| 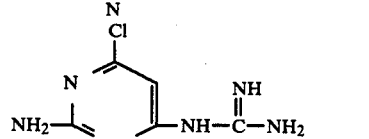 NH₂—[4-Cl-pyrimidin-2-yl]—NH—C(=NH)—NH₂ | | 30.0 | 8 | 56.76* | 201.53* | 0.281* |
| | | 60.0** | 8 | 66.58* | 81.06 | 0.824* |
| | | 60.0 | 8 | 220.62* | 249.64* | 0.867* |
| | | 120.0** | 8 | 260.30* | 59.32 | 4.392* |
| | | 120.0** | 8 | 186.98* | 79.81 | 2.276* |

*significant
**side effects such as ptosis, antidiuresis

As an indication of the criticality of the substitution pattern on the pyrimidine ring the following compounds were inactive in the sodium deficient rat at similar doses: 2-guanidino-4-methylamino-6-chloropyrimidine; 2-guanidino-4,5-diaminopyrimidine; 2-guanidino-4-amino-5,6-dichloropyrimidine; 2,6-dichloro-4-guanidinopyrimidine.

In the smae pharmacological procedure a well known diuretic compound, hydrochlorothiazide, gave the following results:

| 5 | — | 31.6 | 355 | 0.0867 |
| 30 | — | 13.64 | 198 | 2.805 |

A potassium sparing diuretic, triamterene, gave the following results:

| 15 | — | 64.9 | 53.4 | 1.213 |
| 30 | — | 154.4 | 56.1 | 2.730 |

From the biological data presented above it will be apparent to those skilled in the art that the new compounds of this invention exhibit natriuresis at middle part of the dose ranges used in the test procedures usually with an increased Na⊕/K⊕ excretion ratio which profile is characteristic of a potassium sparing diuretic agent. Oral doses of the compounds selected from the range of 10–120 mg/kg (indicating weight of base/body weight) have a natriuretic activity. Most pronounced activity without limiting side effects was detected at doses selected from range of 15–60 mg/kg.

The pharmaceutical compositions of this invention containing a compound of Formula I which has diuretic activity are prepared in conventional dosage unit forms by incorporating the chemical compound, or a pharmaceutically acceptable acid addition salt thereof, with a nontoxic pharmaceutical carrier according to accepted procedures. A nontoxic quantity of said active ingredient is chosen which is sufficient to produce the desired pharmacodynamic activity in a subject, animal or human without unacceptable toxicity. The compositions will contain the active ingredient in such an active but nontoxic amount selected from about 75 mg to about 500 mg of active base ingredient per dosage unit but this quantity depends on the specific biological activity desired, the activity of the compound and the conditions of patient.

A wide variety of pharmaceutical forms can be employed. Thus, if a solid carrier for oral administration is used the preparation can be tableted, placed in a hard gelatin capsule in powder or pellet form, or in the form of a suppository, trouche or lozenge. The amount of solid carrier will vary widely but preferably will be from about 25 mg to about 1 g. If a liquid carrier is used, the preparation will be in the form of a syrup, emulsion, soft gelatin capsule, sterile injectable liquid such as an ampul, or an aqueous or nonaqueous liquid suspension.

The pharmaceutical preparations are made following the conventional techniques of the pharmaceutical chemist involving mixing, granulating and compressing when necessary, or variously mixing and dissolving the ingredients as appropriate to give the desired end product.

The method of producing diuretic activity comprises administering internally to a patient in need of such activity a compound of Formula I or a pharmaceutically acceptable acid addition salt thereof, usually combined with a pharmaceutical carrier, in a nontoxic amount sufficient to produce said activity as described above. The route of administration may be any route which effectively transports the active compound to the site of action which is to be affected within the kidney such as orally or parenterally. Advantageously, equal oral doses will be administered several times such as from 2-5 times a day with the daily dosage regimen being selected from about 150 mg to about 1.5 g.

The following examples are designed solely to illustrate the preparation and use of the compounds of this invention. The temperatures are Centigrade. The doses outlined herein are in terms of the base form of the compounds of Formula I. Other variations of these examples will be obvious to those skilled in the art.

EXAMPLE 1

A solution of 141.8 g (1.48 mole) of guanidine hydrochloride, 59.3 g (1.48 m) of sodium hydroxide and 709 ml of water was added to a solution of 183.4 g (0.74 m) of 2,4,6-trichloropyrimidine in 2127 ml of acetone causing a mild exothermic reaction. After stirring for 1 hour at room temperature, a mixture of solid and oil had formed. Refrigeration caused complete crystallization. The crystals were filtered, then suspended in 1200 ml of water and stirred for 1 hour, filtered, washed with water, then acetone and air dried to give 53.0 g (35%) of 4,6-dichloro-2-guanidinopyrimidine, mp > 360°.

Anal. Calcd. for $C_5H_5Cl_2N_5$: C, 29.15; H, 2.45; N, 33.99. Found: C, 29.42; H, 2.43; N, 33.75.

A slurry of 20.0 g (0.097 m) of the dichloro compound in 1000 ml of absolute ethanol was prepared in a stainless steel bomb. The slurry was then cooled to 0° and saturated with ammonia. The bomb was sealed then heated while the contents were stirred at 115° for 16 hours. After cooling, the reaction mixture was concentrated to a viscous dark oil. The oil was dissolved in a small volume of hot methanol; then chilled to give 6.5 g of tan precipitate. The precipitate was recrystallized twice from methanol giving 1.95 g which was dissolved in warm methanol, diluted with ether, made acid with ethereal hydrogen chloride and more ether added. The precipitated white solid was separated by filtration, washed with ether and vacuum dried to give 2.03 g (8.1%) of 4-amino-6-chloro-2-guanidinopyrimidine dihydrochloride, mp 241°-245°.

Anal. Calcd. for $C_5H_6N_6.2HCl$: C, 23.14; H, 3.50; N, 32.31. Found: C, 23.51; H, 3.58; N, 32.00.

Substituting known 2,4,6-tribromopyrimidine or 2,4-dichloro-6-fluoropyrimidine in stoichiometric quantities in the above reactions gives 4-amino-6-bromo-2-guanidinopyrimidine dihydrochloride and 4-amino-6-fluoro-2-guanidinopyrimidine dihydrochloride.

EXAMPLE 2

The combined methanolic mother liquors from the recrystallization of 4-amino-6-chloro-2-guanidinopyrimidine from Example 1 were concentrated to a small volume, then diluted with ether, acidified with ethereal hydrogen chloride, more ether added and chilled. The tan precipitate was collected, then triturated with 500 ml of boiling ethanol, filtered while hot and vacuum dried giving 2.05 g (9.0%) of light gray 4,6-diamino-2-guanidinopyrimidine hydrochloride, m.p. 274° (dec.).

Anal. Calcd. for $C_5H_9N_7.1.85HCl$: C, 25.60; H, 4.66; N, 41.79. Found: C, 25.37; H, 4.71; N, 41.98.

EXAMPLE 3

A mixture of 12.0 g (0.0732 m) of 2-amino-4,6-dichloropyrimidine and 55.0 g (0.931 mole) of guanidine was heated at 80° for 1.5 hours. The mixture was cooled to room temperature and diluted with water; the white crystalline precipitate was filtered, washed with water then air dried giving 7.22 g (53%) of 2-amino-6-chloro-4-guanidinopyrimidine, mp 220° (dec.).

Anal. Calcd. for $C_5H_7ClN_6$: C, 32.18; H, 3.78; N, 45.04. Found: C, 32.08; H, 3.97; N, 45.43.

EXAMPLE 4

A solution of 3.0 g (0.0161 mole) of 2-amino-6-chloro-4-guanidinopyrimidine in a mixture of 100 ml of ethanol and 100 ml of water containing 3.0 g of magnesium oxide and 0.5 g of 10% palladium on charcoal was hydrogenated at room temperature for 2.5 hours at 2.58 KPS. The mixture was filtered, concentrated and the residue converted to the hydrochloride in methanol-ether giving 2.32 g (66%) of 2-amino-4-guanidinopyrimidine hydrochloride. Recrystallization from a mixture of methanol-ethanol gave a melting point of 290° (dec.).

Anal. Calcd. for $C_5H_8N_6.1.8$ HCl: C, 27.58; H, 4.54; N, 38.59. Found: C, 27.44; H, 4.58; N, 38.48.

EXAMPLE 5

A mixture of 9.75 g (0.05 m) of 4,6-dichloro-2-guanidinopyrimidine, 2.95 g (0.05 m) of guanidine base and 200 ml of methanol is heated at reflux for 8 hours. Cooling, filtration and evaporation gives crude 6-chloro-2,4-diguanidinopyrimidine. The crude product is taken up in ethanol and reacted with hydrogen chloride gas to give the dihydrochloride salt.

EXAMPLE 6

A mixture of 2.2 g of 6-chloro-2,4-diguanidinopyrimidine and 250 ml of 2-methoxymethanol is hydrogenated as in Example 4 above to give 2,4-diguanidinopyrimidine isolated and purified as the hydrobromide salt.

EXAMPLE 7

A mixture of 1.7 g (0.01 m) of 4,6-diamino-2-guanidinopyrimidine prepared as in Example 2, 0.9 g (0.01 m) of S-methylisothiourea and 150 ml of methanol is heated at reflux overnight. Evaporation of the volatiles gives 6-amino-2,4-diguanidinopyrimidine.

EXAMPLE 8

| Ingredient | Mg. per Tablet |
|---|---|
| 4-Amino-6-chloro-2-guanidinopyrimidine hydrochloride | 125 (base) |
| Corn starch | 30 |
| Polyvinylpyrrolidone | 12 |
| Magnesium stearate | 3 |
| Corn starch | 16 |

The first two ingredients are mixed and granulated. The granules are dried, mixed with the remaining ingre-

What is claimed is:

1. A basic compound of the formula:

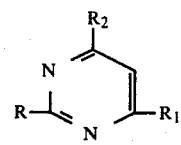

in which:

R and $R_1$ are guanidino or amino, at least one being guanidino; and $R_2$ is hydrogen, halo or amino; together with the pharmaceutically acceptable acid addition salts thereof.

2. The compound of claim 1 in which $R_2$ is halo.
3. The compound of claim 1 in which $R_2$ is amino.
4. The compound of claim 1 in which $R_2$ is chloro.
5. The compound of claim 1 in which R is guanidino and $R_1$ is amino.
6. The compound of claim 1 being 4-amino-6-chloro-2-guanidinopyrimidine or one of its pharmaceutically acceptable acid addition salts.
7. The compound of claim 1 being 4-amino-6-chloro-2-guanidinopyrimidine in the form of its hydrochloride salt.
8. The compound of claim 1 being 2-amino-6-chloro-4-guanidinopyrimidine or one of its pharmaceutically acceptable acid addition salts.
9. A pharmaceutical composition for inducing diuretic activity comprising a diuretic nontoxic quantity of a compound of claims 1, 2, 3, 4, 5, 6, 7 or 8 and a carrier therefor.
10. The composition of claim 9 in which the quantity of the compound is selected from the range of 75–500 mg.
11. The method of inducing diuretic activity in a patient in need therefor comprising administering orally or by injection a nontoxic diuretic quantity of a compound of claims 1, 2, 3, 4, 5, 6, 7 or 8.